US00PP15708P2

(12) United States Plant Patent
Robb

(10) Patent No.: US PP15,708 P2
(45) Date of Patent: Mar. 29, 2005

(54) LAVENDER PLANT NAMED 'PARIS BLUE'

(50) Latin Name: *Lavandula dentata*
Varietal Denomination: Paris Blue

(75) Inventor: John B. Robb, Kariong (AU)

(73) Assignee: Paradise Seed Company, Kulnura (AU)

( * ) Notice: Subject to any disclaimer, the term of this patent is extended or adjusted under 35 U.S.C. 154(b) by 0 days.

(21) Appl. No.: 10/822,986

(22) Filed: Apr. 13, 2004

(51) Int. Cl.[7] ..... A01H 5/00
(52) U.S. Cl. ..... Plt./226
(58) Field of Search ..... Plt./226, 263

(56) References Cited

U.S. PATENT DOCUMENTS

PP9,119 P * 4/1995 Schofield ..... Plt./226
PP14,510 P2 * 2/2004 McNaughton ..... Plt./226

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of Lavender plant named 'Paris Blue', characterized by its compact, upright, somewhat outwardly spreading and mounded plant habit; freely branching, dense and bushy plant form; and violet blue-colored flowers with showy violet blue-colored terminal flower bracts.

1 Drawing Sheet

Botanical classification/cultivar designation: *Lavandula dentata* cultivar Paris Blue.

BACKGROUND OF THE INVENTION

The present Invention relates to a new and distinct cultivar of Lavender plant, botanically known as *Lavandula dentata,* and hereinafter referred to by the name 'Paris Blue'.

The new Lavender is a product of a planned breeding program conducted by the Inventor in Kulnura, New South Wales, Australia. The objective of the breeding program was to create new compact and freely branching Lavender cultivars with large and attractive flowers and good garden performance.

The new Lavender originated from a cross-pollination made by the Inventor in August, 1999, of a unnamed selection of *Lavandula dentata* var. *candicans,* not patented, as the female, or seed, parent with an unnamed selection of *Lavandula dentata,* not patented, as the male, or pollen, parent. The new Lavender was discovered and selected by the Inventor as a single flowering plant within the progeny of the stated cross-pollination grown in a controlled environment in Kulnura, New South Wales, Australia in 1999.

Asexual reproduction of the new cultivar by terminal cuttings taken at Kulnura, New South Wales, Australia, since October, 2000, has shown that the unique features of this new Lavender are stable and reproduced true to type in successive generations.

SUMMARY OF THE INVENTION

Plants of the cultivar Paris Blue have not been observed under all possible environmental conditions. The phenotype may vary somewhat with variations in environment such as temperature and light intensity without, however, any variance in genotype.

The following traits have been repeatedly observed and are determined to be the unique characteristics of 'Paris Blue'. These characteristics in combination distinguish 'Paris Blue' as a new and distinct cultivar:

1. Compact, upright, somewhat outwardly spreading and mounded plant habit.
2. Freely branching, dense and bushy plant form.
3. Violet blue-colored flowers with showy violet blue-colored terminal flower bracts.

Plants of the new Lavender are most similar to plants of the female parent, the unnamed selection of *Lavandula dentata* var. *candicans.* Plants of the new Lavender differ from plants of the female parent selection in the following characteristics:

1. Plants of the new Lavender are more compact than plants of the female parent selection.
2. Plants of the new Lavender and the female parent selection differ in leaf and flower coloration as plants of the female parent selection had light green-colored foliage, green-colored petals and light purple-colored terminal flower bracts.
3. Plants of the new Lavender had shorter peduncles than plants of the female parent selection.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Lavender.

The photograph at the bottom of the sheet comprises a side perspective view of a typical flowering plant of 'Paris Blue' grown in a one-gallon container.

The photograph at the top of the sheet comprises a close-up view of typical leaves and inflorescences of 'Paris Blue'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the winter in a polycarbonate-covered greenhouse in Lompoc, Calif. for about 37 weeks in 1-gallon containers. During the production of the plants, day temperatures ranged from 18 to 24° C., night temperatures ranged from 16 to 18° C., and light levels ranged from 4,000 to 8,000 foot-candles.

Botanical classification: *Lavandula dentata* cultivar Paris Blue.

Parentage:

*Female parent.*—An unnamed selection of *Lavandula dentata* var. *candicans,* not patented.

*Male parent.*—Unnamed selection of *Lavandula dentata,* not patented.

Propagation:

*Type cutting.*—Terminal vegetative cuttings.

*Time to initiate roots.*—Summer: About one week at 25° C. Winter: About two weeks at 20° C.

*Time to produce a rooted young plant.*—Summer: About six weeks at 25° C. Winter: About seven weeks at 20° C.

*Root description.*—Fine, fibrous, and freely branching.

Plant description:

*Form.*—Perennial. Compact, upright, somewhat outwardly spreading and mounded plant form. Freely branching, about twelve main stems each with about three to four lateral branches; dense and bushy plant habit; vigorous growth habit. Flowers in verticillasters on crowded spikes with showy terminal flower bracts.

*Plant height.*—About 32 cm.

*Plant width.*—About 38 cm.

*Lateral branch description.*—Length: About 30 cm. Diameter: About 4 mm. Internode length: About 1.7 cm. Strength: Strong. Aspect: Mostly upright. Texture: Pubescence. Color: 148B.

*Foliage description.*—Arrangement: Opposite, simple; sessile. Length: About 3.5 cm. Width: About 8 mm. Shape: Linear. Apex: Nearly round. Base: Attenuate, clasping. Margin: Scalloped; deeply lobed. Texture, upper and lower surfaces: Pubescence. Fragrance: Very aromatic, pungent. Venation pattern: Pinnate. Color: Developing foliage, upper and lower surfaces: Close to 191A. Fully expanded foliage, upper and lower surfaces: 189A. Venation, upper and lower surfaces: 194A.

Flower description:

*Flower arrangement and shape.*—Small single flowers in compact verticillasters on crowded spikes. Freely flowering, about 90 open flowers and flower buds per spike; flowers tubular with five lobes; inflorescences with showy terminal bracts.

*Natural flowering season.*—Continuous throughout The Spring.

*Flower longevity on the plant.*—Individual inflorescences last about two weeks on the plant and individual flowers last about three to four days on the plant. Flowers not persistent, terminal flower bracts persistent.

*Flower buds.*—Length: About 1 cm. Diameter: About 2.5 mm. Shape: Oblong. Color: 92A.

*Inflorescence size.*—Length: About 3.7 cm. Diameter: About 1.5 cm.

*Flowers.*—Length: About 4 mm. Width: About 4 mm. Depth (height): About 1.1 cm.

*Petals.*—Arrangement: Five, fused into a tube. Length, lobes: About 2 mm. Width, lobes: About 1 mm. Shape: Roughly spatulate. Apex: Rounded. Margin: Entire. Texture, upper and lower surfaces: Smooth, velvety. Color: When opening, upper surface: 92A. When opening, lower surface: 94D. Fully opened, upper surface: 91A. Fully opened, lower surface: 91A; towards the margins, 91C.

*Terminal flower bracts.*—Arrangement: About eight in two whorls at inflorescence apex. Length: About 8 mm. Width: About 6 mm. Shape: Elliptic. Apex: Acute. Base: Attenuate. Margin: Entire. Texture, upper and lower surfaces: Smooth. Color, immature, upper and lower surfaces: 155A. Color, mature, upper and lower surfaces: 91A to 91B.

*Flower bracts.*—Arrangement: Each whorl of flowers subtended by a flower bract. Length: About 1 cm. Width: About 8 mm. Shape: Elliptic to obovate. Apex: Acute. Base: Attenuate. Margin: Entire. Texture, upper and lower surfaces: Smooth. Color, upper and lower surfaces: 198A.

*Calyx.*—Arrangement: Five sepals fused into a tube. Length: About 5 to 7 mm. Width: About 3 mm. Sepal apex: Rounded. Color, upper and lower surfaces: 194A.

*Peduncle.*—Strength: Strong. Length: About 14 cm. Diameter: About 3 mm. Aspect: Mostly upright. Color: 191A. Texture: Smooth.

*Reproductive organs.*—Stamens: Quantity per flower: Four. Anther shape: Oval. Anther length: Less than 1 mm. Anther color: 23A. Pollen amount: Scarce. Pollen color: 23A. Pistils: Quantity per flower: One. Pistil length: About 3 mm. Stigma shape: Rounded. Stigma color: 90A. Style length: About 1.5 mm. Style color: 155A. Ovary color: 145D.

*Seed/fruit.*—Seed and fruit production has not been observed.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from −2 to 40° C.

It is claimed:

1. A new and distinct cultivar of Lavender plant named 'Paris Blue', as illustrated and described.

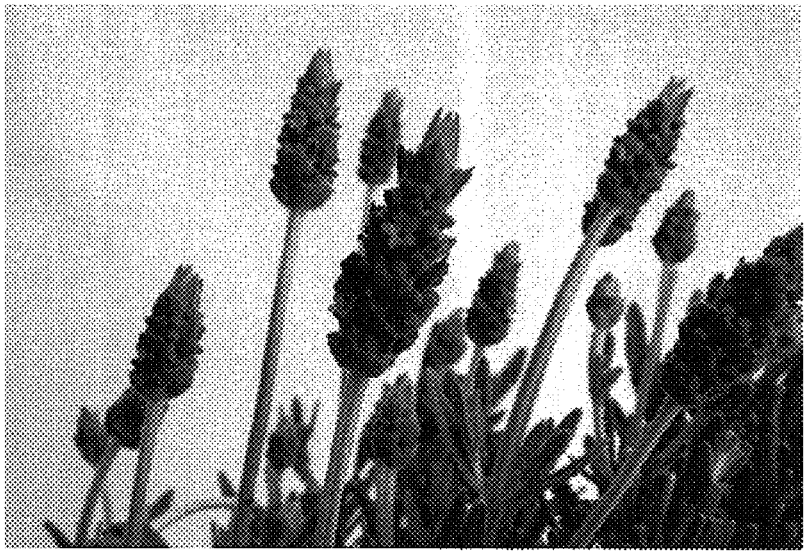
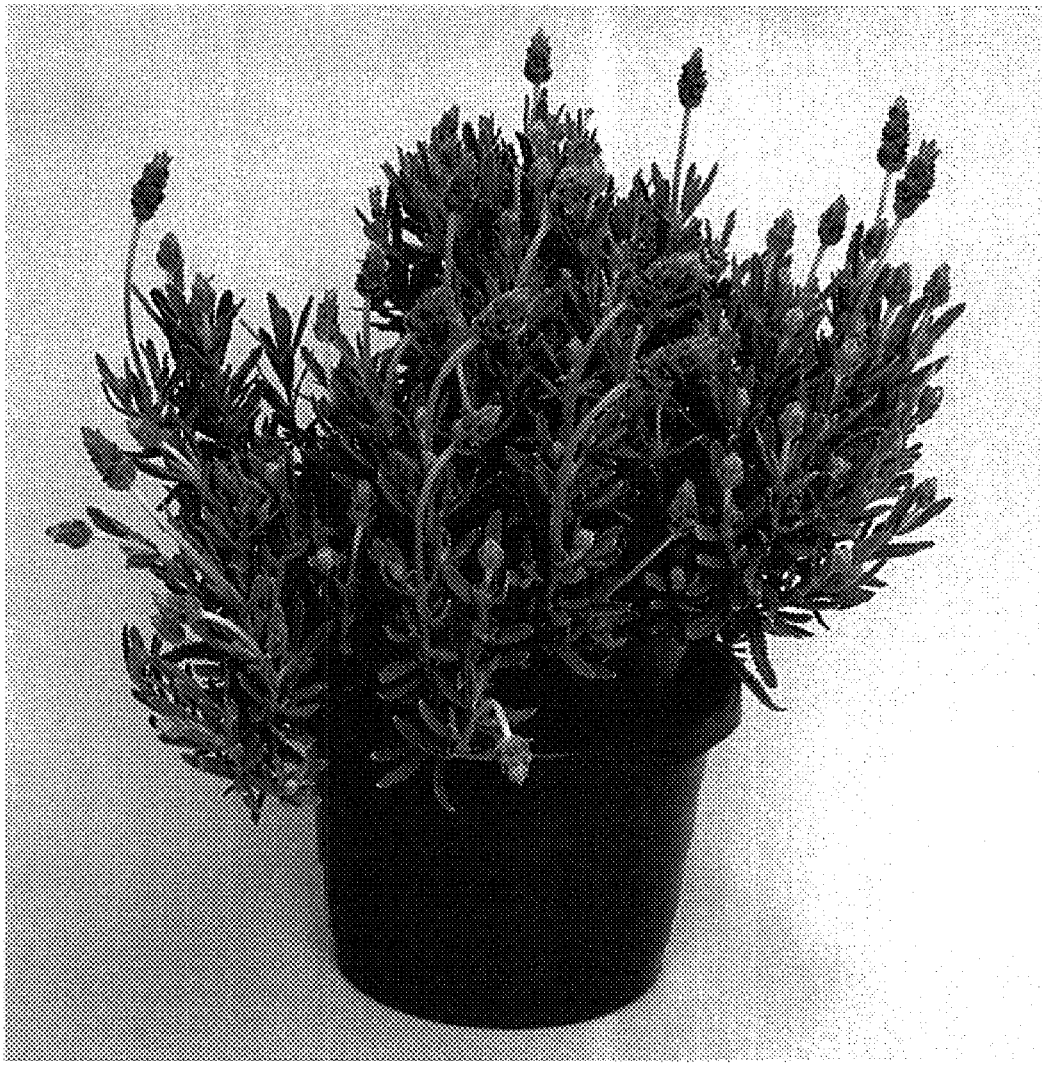

* * * * *